United States Patent
Amano et al.

[11] Patent Number: 6,042,549
[45] Date of Patent: Mar. 28, 2000

[54] EXERCISE INTENSITY MEASURING DEVICE AND EXERCISE QUANTITY MEASURING DEVICE

[75] Inventors: Kazuhiko Amano, Suwa; Kazuo Uebaba, Yokohama; Hitoshi Ishiyama, Toride, all of Japan

[73] Assignee: Seiko Epson Corporation, Tokyo, Japan

[21] Appl. No.: 08/952,943

[22] PCT Filed: Mar. 21, 1997

[86] PCT No.: PCT/JP97/00928

§ 371 Date: Jan. 23, 1998

§ 102(e) Date: Jan. 23, 1998

[87] PCT Pub. No.: WO97/35514

PCT Pub. Date: Oct. 2, 1997

[30] Foreign Application Priority Data

Mar. 22, 1996 [JP] Japan .................................... 8-066926
Apr. 8, 1996 [JP] Japan .................................... 8-085556

[51] Int. Cl.$^7$ ...................................................... A61B 5/02
[52] U.S. Cl. .......................................... 600/500; 600/503
[58] Field of Search ................................... 600/500, 501, 600/502, 503, 481, 490

[56] References Cited

U.S. PATENT DOCUMENTS

| | | |
|---|---|---|
| 4,408,613 | 10/1983 | Relyea . |
| 4,525,074 | 6/1985 | Murakami .................................. 368/10 |
| 5,603,330 | 2/1997 | Suga ........................................ 600/500 |
| 5,749,366 | 5/1998 | Odagiri et al. ........................... 600/503 |
| 5,769,755 | 6/1998 | Henry et al. .................................. 482/8 |
| 5,776,070 | 7/1998 | Kitazawa et al. ........................ 600/483 |
| 5,906,581 | 5/1999 | Tsuda ....................................... 600/500 |

FOREIGN PATENT DOCUMENTS

| | | |
|---|---|---|
| 0 659 384 | 6/1995 | European Pat. Off. . |
| 2-139607 | 11/1990 | Japan . |
| 6-105829 | 4/1994 | Japan . |
| 6-245912 | 9/1994 | Japan . |
| 7-227383 | 8/1995 | Japan . |
| 8-10234 | 1/1996 | Japan . |
| WO 90/12538 | 11/1990 | WIPO . |
| WO 91/18550 | 12/1991 | WIPO . |

*Primary Examiner*—Cary O'Connor
*Assistant Examiner*—Navin Natnithithadha

[57] ABSTRACT

An exercise intensity and exercise quantity measuring device is disclosed, which is capable of measuring the exercise intensity, irrespective of the type, of exercise, and measuring the exercise quantity only when the user is carrying out exercise of suitable intensity. The user first estimates his $Vo_{2max}$ in advance by the conventional direct method, and inputs this value into the device. The device determines upper and lower limit values of pulse rate corresponding to this $Vo_{2max}$. During the time of exercise when pulse rate is between the upper and lower limit values, CPU 308 increments the accumulated time stored in RAM 309, at intervals based on a clock pulse supplied by oscillation circuit 311 and frequency dividing circuit 312. At the same time, CPU 308 compares the pulse waveform during exercise and the pulse waveform at rest, and estimates the exercise intensity.

22 Claims, 17 Drawing Sheets

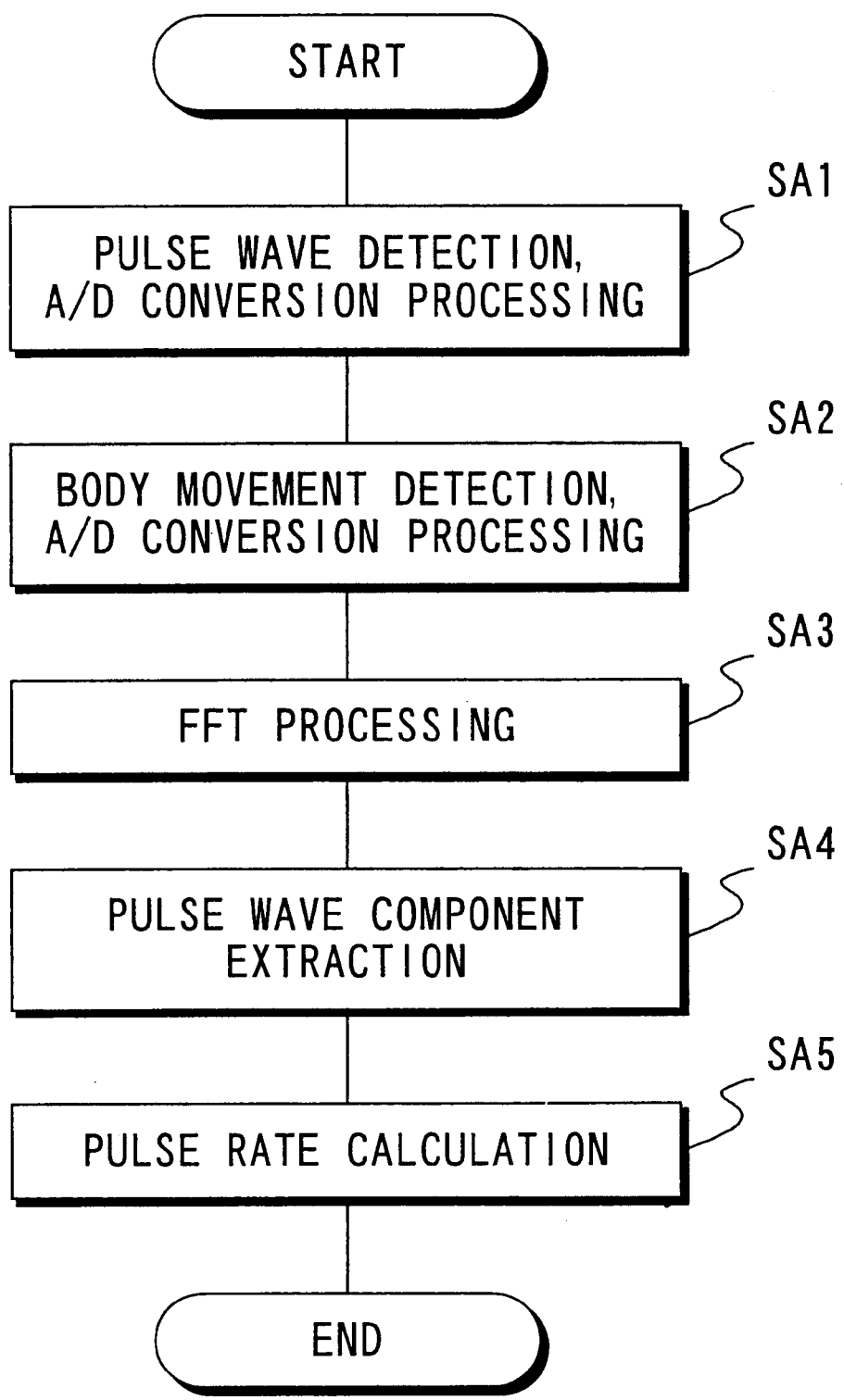

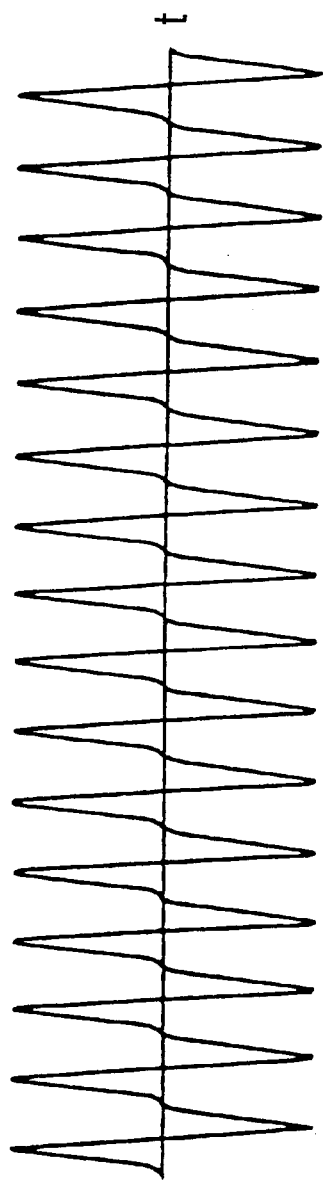
FIG. 4A ORIGINAL WAVEFORM
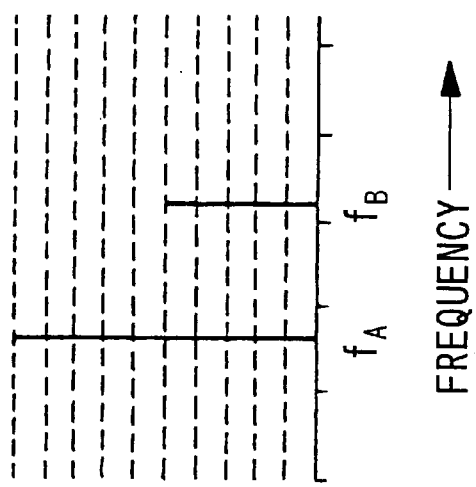
FIG. 4B

| VO$_{2max}$ | 36 | 37 | 38 | 39 | 40 | 41 | 42 |
|---|---|---|---|---|---|---|---|
| PULSE RATE | 105 | 110 | 115 | 120 | 125 | 130 | 135 |

| OPTIMAL EXERCISE INTENSITY | 750 kpm/MIN |
|---|---|
| EXERCISE FREQUENCY | 3 TIMES/WK |
| EXERCISE DURATION | 20 MIN |

EXERCISE INTENSITY MEASURING DEVICE AND EXERCISE QUANTITY MEASURING DEVICE

BACKGROUND OF THE INVENTION

1. Field of the Invention

The present invention is concerned with device for measuring exercise intensity and with a device for measuring exercise quantity during exercise such as running, race walking, and so on.

2. Background Art

Many people do exercise for promoting their health.

In general, an individual performing exercise (hereafter, referred to as an exerciser) ascertains his own exercise capacity and then carries out exercise of an intensity depending on his capacity.

However, even when the intensity of the exercise is the same, the stress loaded on the body will vary each time, depending on the condition of the body.

For this reason, even when the exerciser exercises in accordance with his own exercise capacity, it is desirable that the exercise should be carried out with constant monitoring of the degree of stress loaded on the exerciser.

Japanese Patent Application First Publication No. Hei 8-10234 (Title: Device for Measuring Exercise Quantity) may be cited as one example of exercise quantity measuring devices developed to meet this purpose.

However, in this exercise quantity measuring device, the sensor for detecting blood flow is fixed in place to the treadmill machine. Thus, considering that exercise intensity is limited only to exercise in which the treadmill is employed, there must be a disadvantage it is not possible to measure exercise intensity during exercise when the treadmill machine is not available.

In addition, a pedometer is available as an example of devices for measuring exercise quantity (note that in this specification, exercise intensity indicates the intensity of exercise at each instant, while exercise quantity indicates the amount of exercise within a given period of time).

However, exercise which falls below a given intensity level has little significance from the perspective of promoting endurance. Conversely, an exercise level which is in excess of a given intensity level may be dangerous. It is therefore necessary that exercise of the appropriate intensity should be performed.

An pedometer typically counts the number of steps, irrespective of whether the user is walking slowly or quickly. While the user is able to know the number of steps, he cannot know how many steps are truly effective (i.e., the exercise quantity).

Furthermore, as an individual continues to do exercise, the appropriate intensity as described above will increase. In this regard, a device capable of measuring the exercise quantity corresponding to the improvement of individual s exercise capacity had not been available until now.

SUMMARY OF THE INVENTION

The present invention was conceived in consideration of the above-described circumstances, and has as its first objective the provision of an exercise intensity measuring device capable of measuring the intensity of exercise, irrespective of the type of exercise being performed.

The present invention has as a second objective the provision of an exercise quantity measuring device which can measure the exercise quantity only for exercise which is of an appropriate intensity for the user.

In order to resolve these objectives, the present invention is firstly characterized in determining the exercise intensity of the exercise currently being performed from the harmonic wave components of the pulse waveform.

Further, the present invention is secondly characterized in the provision of:

a pulse rate setting means which sets the appropriate limits for the pulse rate during exercise based on maximal oxygen uptake quantity, $\%\text{Vo}_{2max}$ by the user;

a pulse rate measuring means which measures the user s pulse rate;

an accumulating means which accumulates the time duration in which the pulse rate measured by the pulse rate measuring means is within the limits set by the pulse rate setting means; and a notifying means which provides notice of the results of the accumulating operation performed by the accumulating means.

As a result of the above described first characteristic, it is possible to measure the intensity of exercise irrespective of the type of exercise being performed.

Further, as a result of the above-described second characteristic, it is possible to measure the exercise quantity only for exercise which is of an appropriate intensity for the user.

BRIEF DESCRIPTION OF THE FIGURES

FIG. 3 is a flow chart showing the method of detection of pulse waveforms by this exercise intensity and exercise quantity measuring device.

FIG. 4A is a figure showing the signal obtained by adding frequency fA and frequency fB; FIG. 4B is a graph showing the results obtained after carrying out FFT processing to this added signal.

PREFERRED EMBODIMENTS OF THE PRESENT INVENTION

Embodiment 1

Preferred embodiments of the present invention will now be explained with reference to the accompanying figures.

1. Structure of the Embodiment

Figure 1:
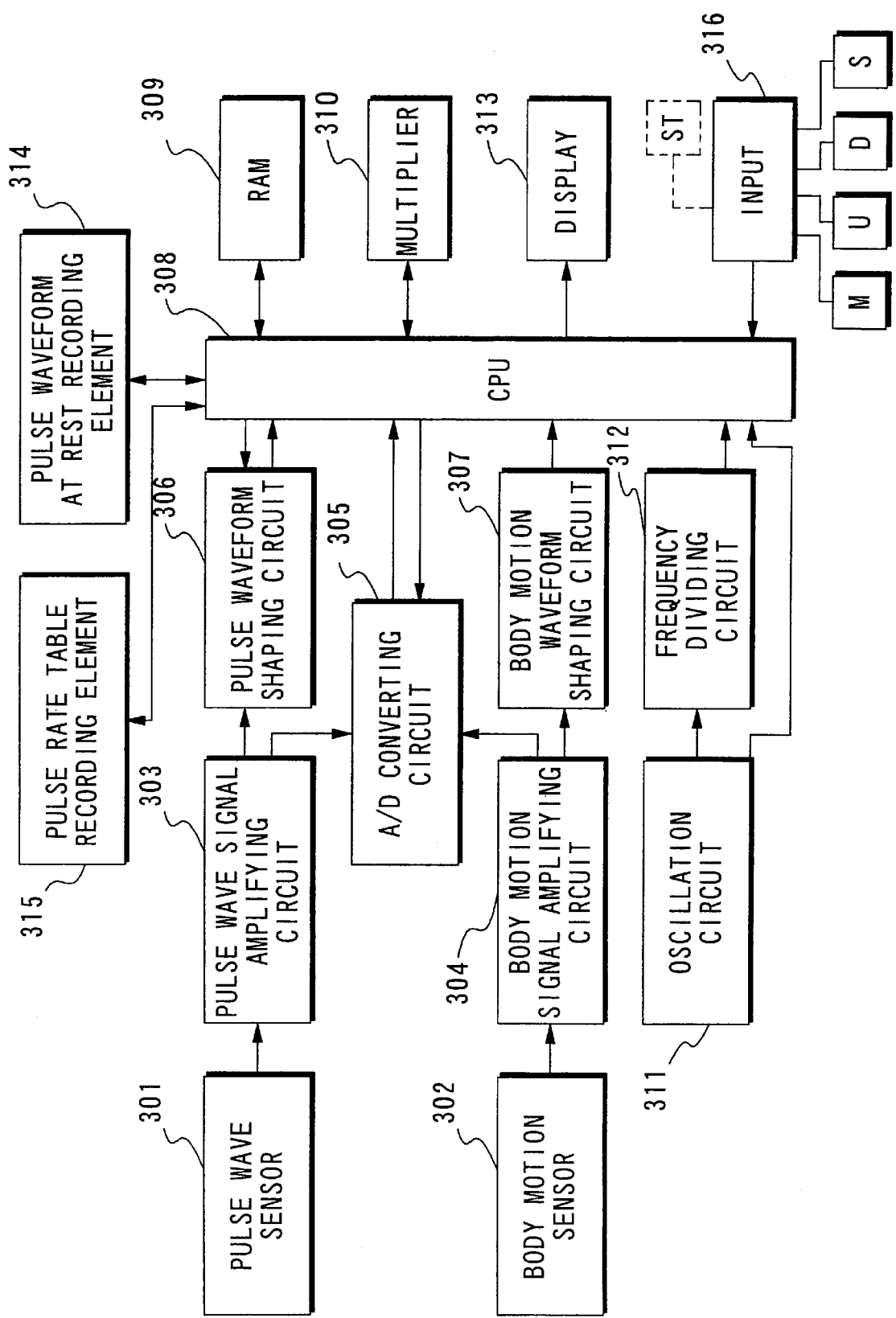
FIG. 1 is a block diagram showing an example of the structure of the exercise intensity and exercise quantity measuring device according to a first embodiment of the present invention.

FIG. 1 is a block diagram showing an example of the structure of the exercise intensity and exercise quantity measuring device according to this embodiment.

In this figure, pulse wave sensor 301 detects the pulse wave in the body, and outputs the detected pulse wave signal to a pulse wave signal amplifying circuit 303. Pulse wave sensor 301 may be a piezoelectric microphone, for example.

Body motion sensor 302 detects body motion, and outputs the detected body motion signal to body motion signal amplifying circuit 304. Body motion sensor 302 may be an acceleration sensor, for example.

Pulse wave signal amplifying circuit 303 amplifies the detected pulse wave signal, and outputs the signal to A/D converting circuit 305 and pulse waveform shaping circuit 306.

Body motion signal amplifying circuit 304 amplifies the detected body motion signal, and outputs the signal to A/D converting circuit 305 and body motion waveform shaping circuit 307.

A/D converting circuit 305 converts the amplified pulse wave signal and body motion signal from analog to digital signals, and outputs this result to Central Processing Unit (CPU) 308.

Pulse waveform shaping circuit 306 shapes the amplified pulse wave signal, and outputs it to CPU 308.

Body motion waveform shaping circuit 307 shapes the amplified body motion signal, and outputs the result to CPU 308.

Pulse waveform at rest recording means 314, which is a non-volatile memory (E²PROM, flash memory, battery backed-up RAM, or the like), records the pulse waveform at rest obtained by CPU 308.

Oscillation circuit 311 generates a fixed period clock pulse.

Frequency dividing circuit 312 divides the clock pulse generated by oscillation circuit 311, and generates a pulse with a specific period.

Display 313, formed of a liquid crystal display, displays the cumulative value for the aforementioned time duration.

Input element 316 has a mode switch M employed for selecting a variety of modes, an up switch U and down switch D employed to change the setting values, and a set switch S employed to determine setting values.

Pulse rate table recording element 315 is formed of ROM (read-only memory), specifically, and stores the pulse rate table.

Figures 16, 17:
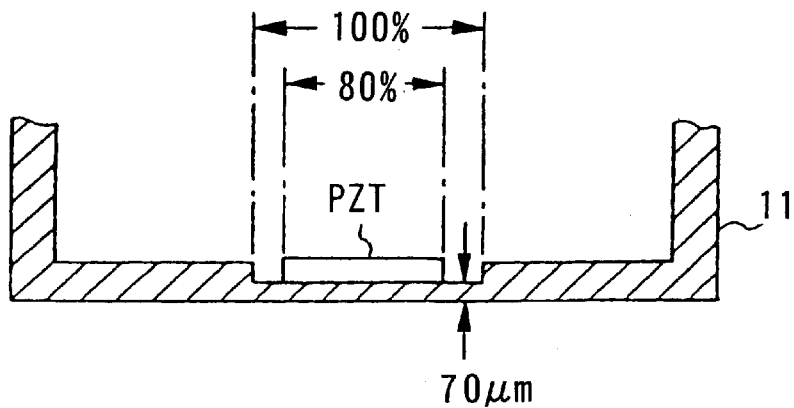
FIG. 16 is a cross-sectional view showing the state of the installment when a piezo element is employed as a notifying means.
FIG. 17 is an explanatory view showing an example of a pulse rate table.

FIG. 17 is an explanatory diagram showing an example of this pulse rate table.

As shown in this figure, the pulse rate table stores the pulse rate corresponding to each $Vo_{2max}$.

In this figure, the $Vo_{2max}$ is the maximal oxygen uptake by a given person when that person is exercising at maximum intensity. Further, in addition to showing maximal uptake of oxygen, $Vo_{2max}$ may also be employed to show the exercise intensity, such as exercise in which $Vo_{2max}$ is 40 ml/kg/min.

In the figure, the pulse rate for each $Vo_{2max}$ is that pulse rate shown by the average person having the $Vo_{2max}$ as indicated, when exercising at an intensity corresponding to 50% of that $Vo_{2max}$.

Note that there are two types of pulse rate tables (for males and females) recorded in pulse rate table recording element 315. The pulse rate table shown in FIG. 17 is for males.

Figure 2:
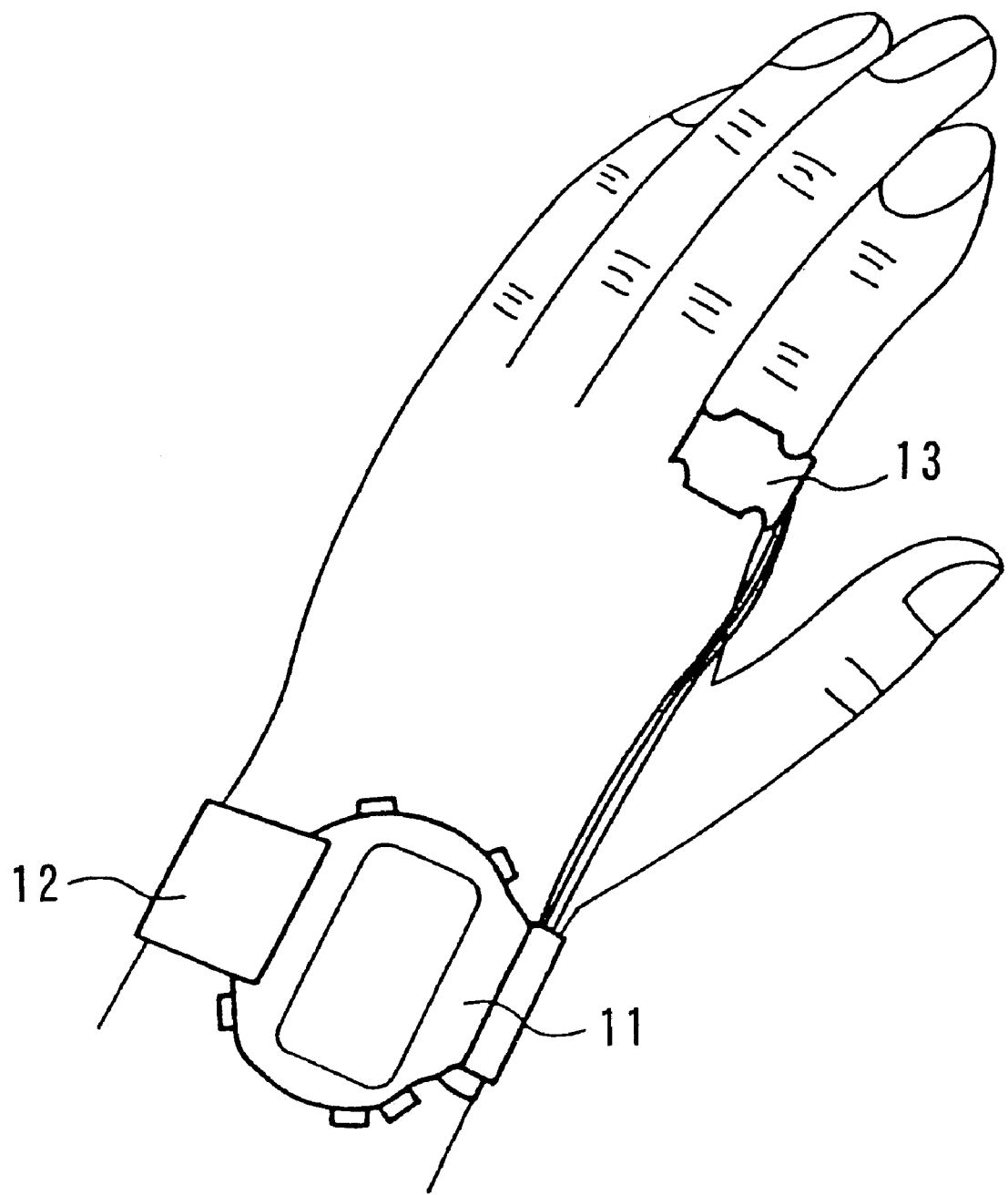
FIG. 2 is a slant view of the outer appearance of the aforementioned exercise intensity and exercise quantity measuring device.

FIG. 2 is a slant view showing the outer appearance of this device.

In this figure, main body 11 is attached to the arm of the user by means of a belt 12.

Pulse wave sensor 301 (see FIG. 1) and body motion sensor 302 (see FIG. 1) are fixed to the finger by finger belt 13.

FIG. 2 is a slant view showing the outer appearance of this device.

In this figure, main body 11 is attached to the arm of the user by means of a belt 12.

Pulse wave sensor 301 (see FIG. 1) and body motion sensor 302 (see FIG. 1) are attached to the finger by means of finger belt 13.

2. Operation of the Embodiment (1) Measurement of $Vo_{2max}$

The operation of the aforementioned exercise intensity and exercise quantity measuring device will now be explained.

The user estimates his own $Vo_{2max}$ in advance using a conventional indirect method. In this case, there is available an indirect method wherein $Vo_{2max}$/wt is estimated from rate and power under maximum exercise (see Insurance Science, Vol. 32, No. 3, 1990.).

Figure 18A:
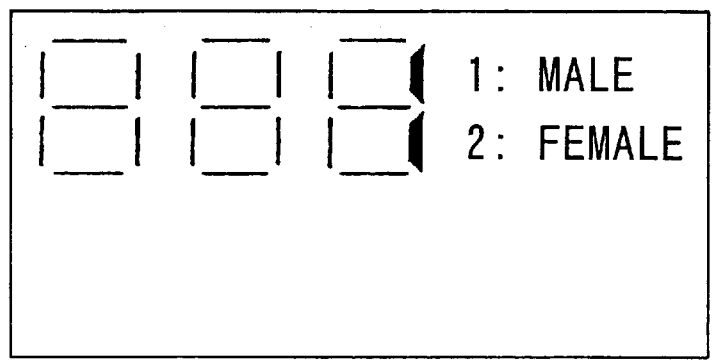
FIGS. 18A and 18B are explanatory figures showing an example of display device 313.

Next, the user presses a mode switch M (see FIG. 1), thereby changing the display on display 313 to the state shown in FIG. 18(a).

In this state, when the user presses the up switch U (or the down switch D) one time, the display on display 313 changes from 1 (male) to 2 (female), or from 2 (female) to 1 (male). After matching the display to his or her sex in this way, the user then inputs the aforementioned value by pressing set switch S. As an example in this case, 1 (male) is input.

Once the sex of the user is input, CPU 308 reads out the pulse rate table corresponding to the input sex from among the two pulse rate tables (for males and females) stored in pulse rate table recording element 315. Since 1 (male) was input in this case, CPU 308 reads out the pulse rate table for males (see FIG. 17).

Figure 18B:
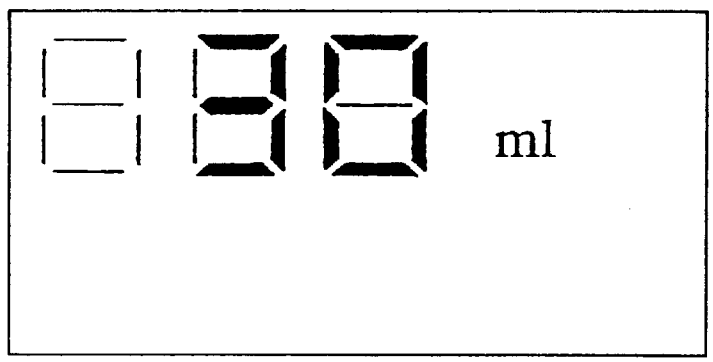

Next, the user presses the mode switch M, causing the display on display 313 to change to the state shown in FIG. 18(b).

In this state, the display on display 313 is counted up when the user continues to press up switch U, or is counted down when the user continues to presses down switch D. Once the user has matched the display to his own $Vo_{2max}$, he inputs this value by pressing set switch S. As an example in this case, 40 is input.

Once $Vo_{2max}$ is input, CPU 308 reads out the pulse rate corresponding to this $Vo_{2max}$ from the pulse rate table read out above (see FIG. 17). Here, since 40 was input, CPU 308 reads out the value 125 corresponding to the aforementioned value 40.

Next, CPU 308 determines the value of the upper limit for pulse rate by multiplying the read out pulse rate by a specific upper limit value coefficient 1.2 (i.e., 120%). In this example, since the aforementioned pulse rate was 125, the value of the upper limit become 150.

Similarly, CPU 308 determines the limit of the lower value for the pulse rate by multiplying the pulse rate read out above by a specific lower limit value coefficient 0.8 (i.e., 80%). In this example, since the aforementioned pulse rate was 125, the value of the lower limit becomes 100.

(2) Collection of data at rest

When the user simultaneously depresses start switch S and mode switch M while at rest subsequent to setting the upper and lower limit values for pulse rate, the device according to this embodiment begins to detect the user s pulse waveforms at rest. This will be explained in greater detail with reference to the flow chart in FIG. 3.

At step SA1 in this figure, the pulse wave is detected, this pulse wave signal is amplified, and the amplified pulse wave signal is converted from an analog to a digital signal.

At step SA2, body motion is detected, this body motion signal is amplified and the amplified body motion signal is converted from an analog to a digital signal.

At step SA3, the analog-to-digital converted pulse wave signal and body motion signal are subjected to Fast Fourier Transform (FFT) processing.

At step SA4, the beat frequency component is extracted based on the FFT processed pulse wave signal and body motion signal.

Beat frequency component as used in this specification is defined as the beat frequency component obtained after removing the frequency component corresponding to the body motion signal from the result obtained after FFT processing of the pulse wave signal. The details of this processing are discussed below under heading (3), Data collection during exercise. However, when the user is at rest, the level of the body motion signal is so low as to be acceptably ignored. For this reason, the beat frequency component is equivalent to the result obtained after FFT processing of the pulse wave signal.

At step SA5, the pulse rate is calculated from the extracted beat frequency component.

When the pulse waveform at rest is detected, CPU 308 records this pulse waveform in pulse waveform at rest recording means 314.

In other words, the fundamental wave component is extracted from among the beat frequency components, and the value obtained after dividing 60 sec by the inverse of the fundamental wave component (i.e., the period of the fundamental wave component) becomes the pulse rate.

FIG. 4A shows the signal obtained after adding frequencies fA and fB (where, however, the amplitude of frequency fB is ½ that of frequency fA). FIG. 4B is a graph showing the result obtained after FFT processing of the added signal.

The lowest frequency obtained as a result of FFT processing is determined according to the inverse of the duration of analysis. For example, if the duration of analysis was 16 sec, then the line spectrum is 1/16 sec. In other words, a resolution of 62.5 msec is obtained. Accordingly, the signal which is subject to analysis is resolved to a harmonic wave component which is an integer multiple of 16 Hz. The size (power) of the respective harmonic components is expressed along the vertical axis. FIG. 4B shows that frequency fB has half the power of frequency fA.

(3) Collection of data during exercise

Figure 7:
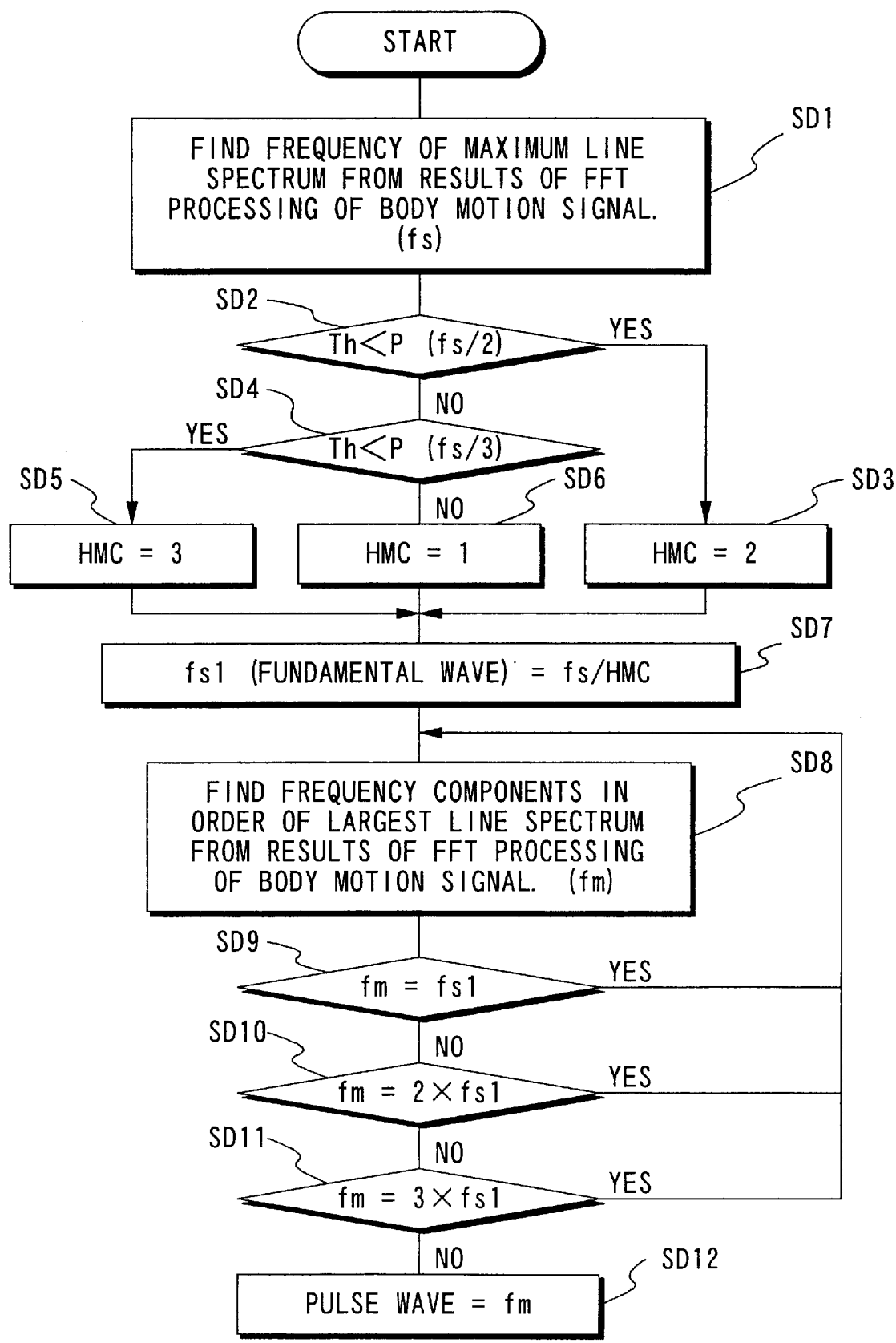
FIG. 7 is a flow chart showing the processing method for specifying the beat frequency component after specifying the harmonic wave of the body motion signal.

When the user presses start switch S during exercise, the routine shown in FIG. 3 is executed repeatedly. As a result, the user s pulse waveform during exercise is detected. Further, the subroutine shown in FIG. 7 is invoked via step SA4 each time the routine shown in FIG. 3 is executed. The details of this subroutine will now be explained.

First, it is necessary to carry out processing to remove the body motion component, since this component overlaps with the pulse wave when the user is exercising.

Figure 5A:
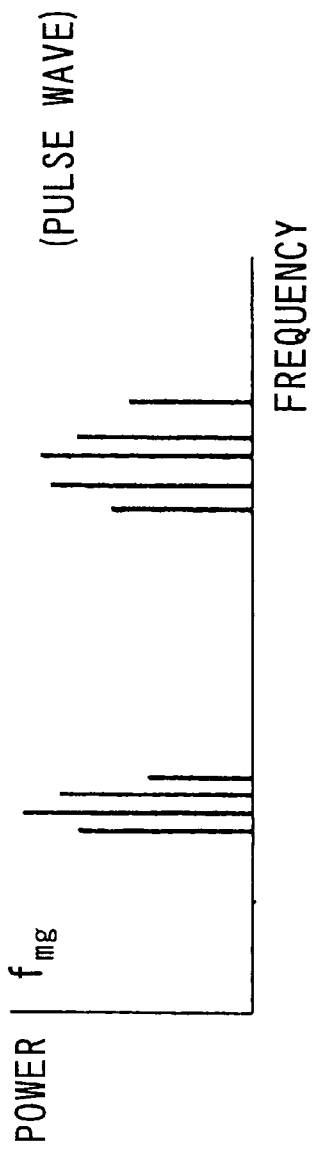
FIGS. 5A to C are graphs showing examples of the results obtained after carrying out FFT on the signal output from body motion sensor 302 and pulse wave sensor 301 when the user is exercising.
Figure 5B:
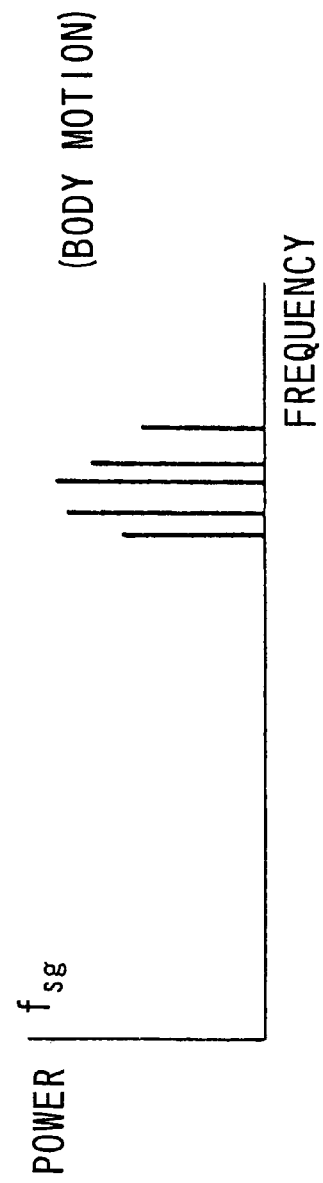
Figure 5C:
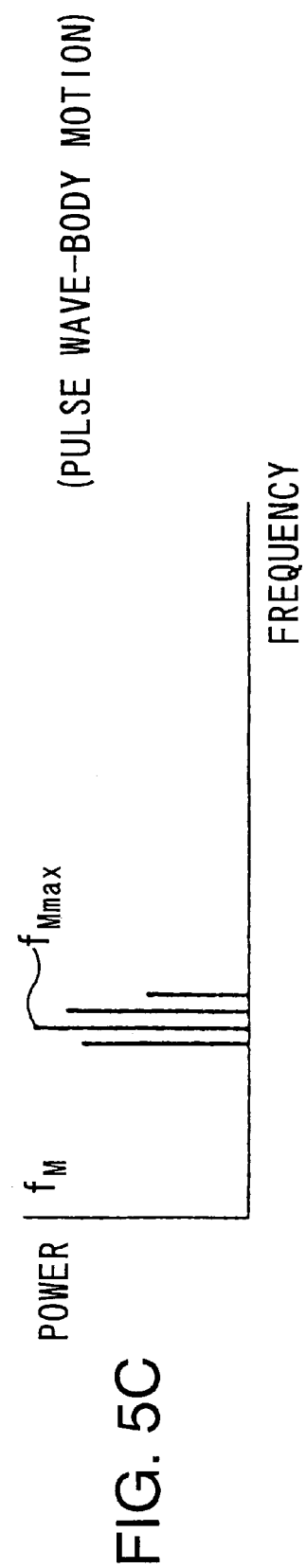

FIG. 5 is a graph showing an example of the results obtained after carrying out FFT processing of the signal output from pulse wave sensor 301 and body motion sensor 302 during exercise. In this figures, 5A shows the result (pulse wave spectrum fmg) obtained after carrying out FFT processing to the signal output from pulse wave sensor 301; 5B shows the result (body motion spectrum fsg) obtained after carrying out FFT processing to the signal output from body motion sensor 302; and 5C shows the beat spectrum fM obtained after subtracting the body motion spectrum fsg from the pulse wave spectrum fmg.

As shown in those figures, the beat frequency component and the frequency component from the signal generated by body motion are both present in 5A.

In contrast, since body motion sensor 302 corresponds to body motion only, only the frequency component from the signal generated by body motion is obtained in 5B.

Accordingly, the body motion spectrum fsg is subtracted from the pulse wave spectrum fmg, and the largest spectrum from among the remaining line spectrum fM is specified as the beat frequency component.

However, in actuality, because of the influence of the harmonic wave signals, it may be difficult to perform analysis of the waveforms output by these respective sensors by means of a method which simply obtains the difference therebetween. Accordingly, a more detained explanation will now be made of the method for specifying the pulse wave.

First we will consider the frequency range for analysis. Ordinarily, the frequency of body motion is 1~2 Hz. Accordingly, if fmax=4 Hz, then a check up through the third harmonic wave is sufficient.

In this embodiment, the maximum body motion component in the 2 to 4 Hz frequency region is extracted, and the maximum component therein is assumed to be the second harmonic wave of the body motion component. This will be explained in greater detail below. Next, the reason for making the assumption will be discussed.

Figure 6:
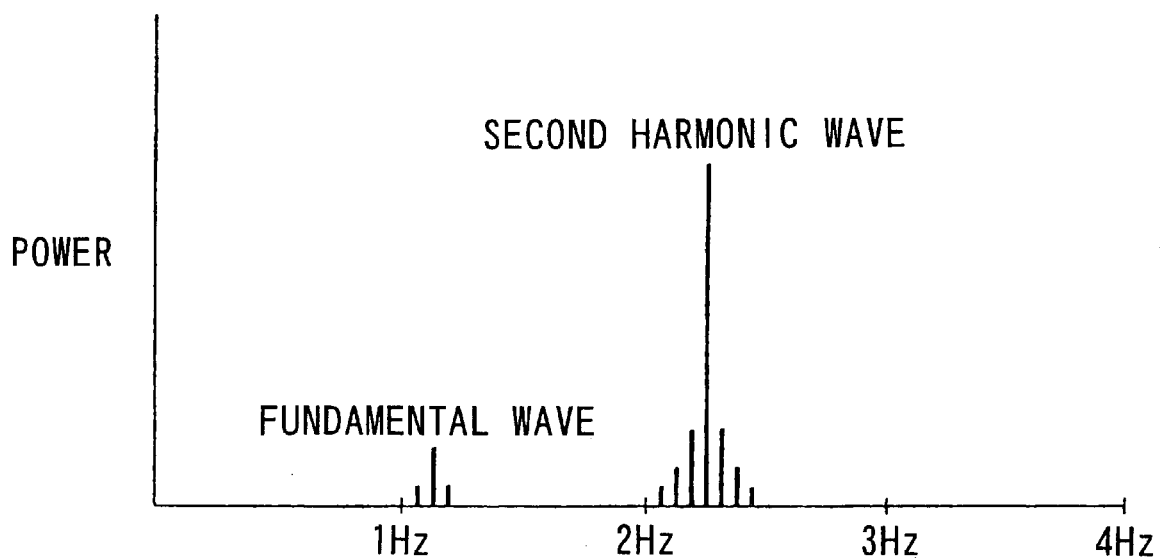
FIG. 6 is the result obtained after carrying out FFT processing on the output of body motion sensor 302.

FIG. 6 shows the results obtained after carrying out FFT processing on the output from body motion sensor 302. In general, when exercising, and particularly, when running, the power of the second harmonic wave becomes higher versus the fundamental wave (an increase of 3 to 10-fold, in the case of normal running, for example), as shown in FIG. 6. The following three factors may be considered when analyzing the factors detected by body motion sensor 302 when the user is running. Namely, 1. upward and downward motion during running
2. the fundamental wave of arm swinging
3. the second harmonic wave of arm swinging With respect to (1), the upward and downward motion appears uniformly when taking a step with the right foot and when taking a step with the left foot, so that this motion becomes the second harmonic wave of the body motion component.

With respect to (2), a pendulum motion is indicated, in which the swinging forward and drawing back motion of the arms constitutes one period. Typically, however, it is difficult to render the swinging of the arms during running into a smooth pendulum motion, while the power of this component is weak.

With respect to (3), because acceleration is applied at the instant the arms swing forward and the instant they are drawn back, the second harmonic wave appears more strongly than the fundamental wave.

Accordingly, within the frequency of body motion, the second harmonic wave component is characteristically obtained.

In the case of ordinary running, given a range of 2 to 4 Hz, it is possible to cover the region in which the second harmonic wave appears, regardless of whether the pace of running is slow or fast. Accordingly, by extracting the characteristic second harmonic wave component after limiting the region in this way, it is possible to increase the accuracy of detection.

FIG. 7 is a flow chart for the subroutine for specifying the pulse wave frequency component after specifying the harmonic wave of the body motion signal. This subroutine is invoked in the aforementioned step SA4.

In step SD1, CPU 308 determines the line spectrum fs at which power P is maximal, based on the results of frequency analysis of the body motion signal.

In steps SD2, CPU 308 decides whether or not a body motion component P(fs/2) above a given fixed value Th is present at a frequency position which is one-half that of frequency fs.

When the result of this determination is YES, i.e., when a body motion component P(fs/2) above a given fixed value Th is present, then processing proceeds to step SD3.

In step SD3, frequency fs is specified as the second harmonic wave (HMC=2).

When the result of the determination in step SD2 is NO, i.e., when a body motion component P(fs/2) above a given fixed value Th is not present, then processing proceeds to step SD4.

In step SD4, CPU 308 decides whether or not a body motion component P(fs/3) above a given fixed value Th is present at a frequency which is ⅓ that of frequency fs.

When the result of this determination is YES, i.e., when a body motion component P(fs/3) above a given fixed value Th is present, then processing proceeds to step SD5.

In step SD5, CPU 308 specifies fs as the third harmonic wave (HMC=3) of body motion.

When the result of the determination in step SD4 is NO, i.e., when a body motion component P(fs/3) above a given fixed value Th is not present, then CPU 308 specifies frequency fs as frequency fs1 of the fundamental wave.

As a result of the preceding processing, it is possible to specify which of the harmonic waves is frequency fs, so that in step SD7, the fundamental wave fs1 of body motion is obtained.

In steps SD8~SD11, using the results of frequency analysis of the pulse wave, a comparison is made between the frequency fm and the body motion frequency for the line spectrums in a sequential order starting with the line spectrum having the largest power P. In this way, a check is made as to whether or not that frequency coincides with the fundamental wave (fs1), second harmonic wave (2×fs1), or third harmonic wave (3×fs1) of the body motion signal.

As a result of this processing, in step SD12, the maximum pulse wave frequency component fm which does not coincide with a body motion component can be extracted.

(4) Overall processing
(4.1) Display of exercise quantity

By repeatedly executing the routine shown in FIG. 3 as described above, the pulse wave frequency component (step SA4) and the pulse rate (step SA5) at the time of exercise are sequentially determined.

Each time the pulse rate is measured, CPU 308 determines whether or not the measured pulse rate is between the upper and lower limit values therefor.

During the time that the pulse rate is between the upper and lower limit values therefor, CPU 308 increments the accumulated time duration stored in RAM 309 at intervals based on the clock pulse supplied by oscillation circuit 311 and frequency dividing circuit 312.

In contrast, when the pulse rate is above upper limit value UL or below lower limit value LL, then CPU 308 suspends incrementing the accumulated time duration stored in RAM 309.

Note that CPU 308 relayed the accumulated time stored in RAM 309 to display element 313 on a fixed cycle, irrespective of the pulse rate. Thus, display element 313 displays the accumulated time. As a result of the above-described processing, then, the exercise quantity can be obtained.
(4.2) Display of exercise intensity Each time that the beat frequency component is measured, CPU 308 reads out the pulse waveform at rest which is stored in pulse wave at rest recording means 314, and estimates the exercise intensity based on the pulse waveform at rest and the beat frequency component of the pulse waveform during exercise.

The method for estimating exercise intensity based on distortion of the beat frequency component of the pulse waveform will now be explained.

Figure 10:
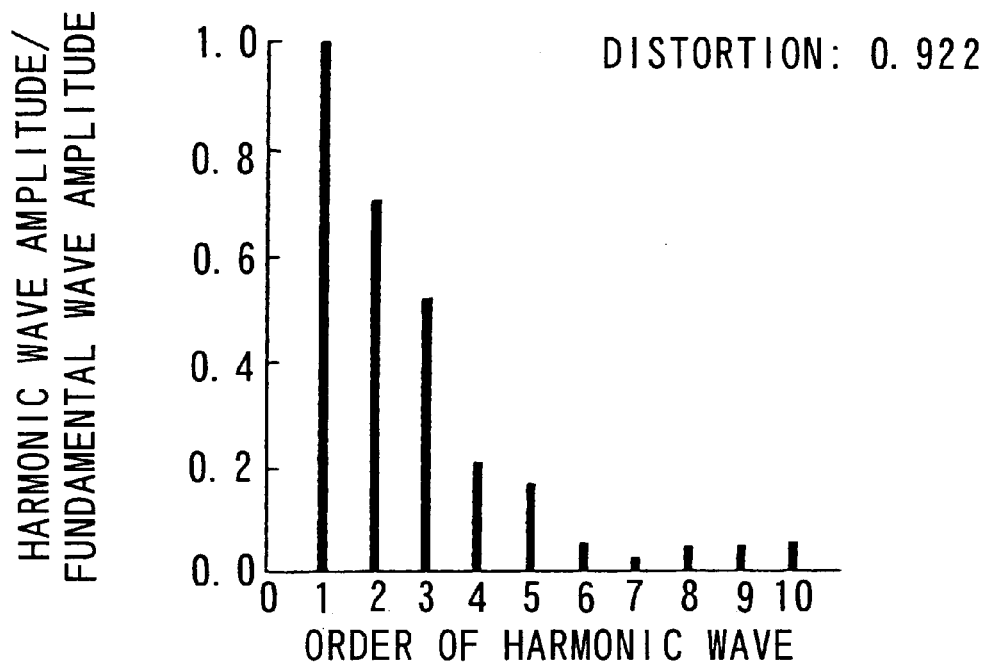
FIG. 10 is a graph showing an example of the frequency line spectrum of a Ping mai or normal pulse.
Figure 11:
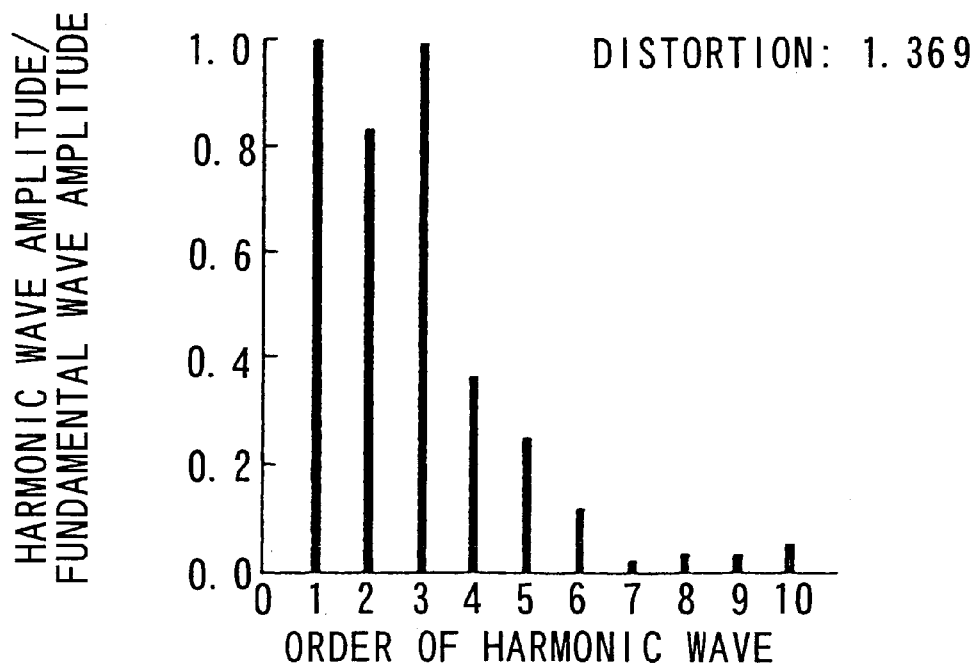
FIG. 11 is a graph showing an example of the frequency line spectrum of a Hua mai or smooth pulse.
Figure 12:
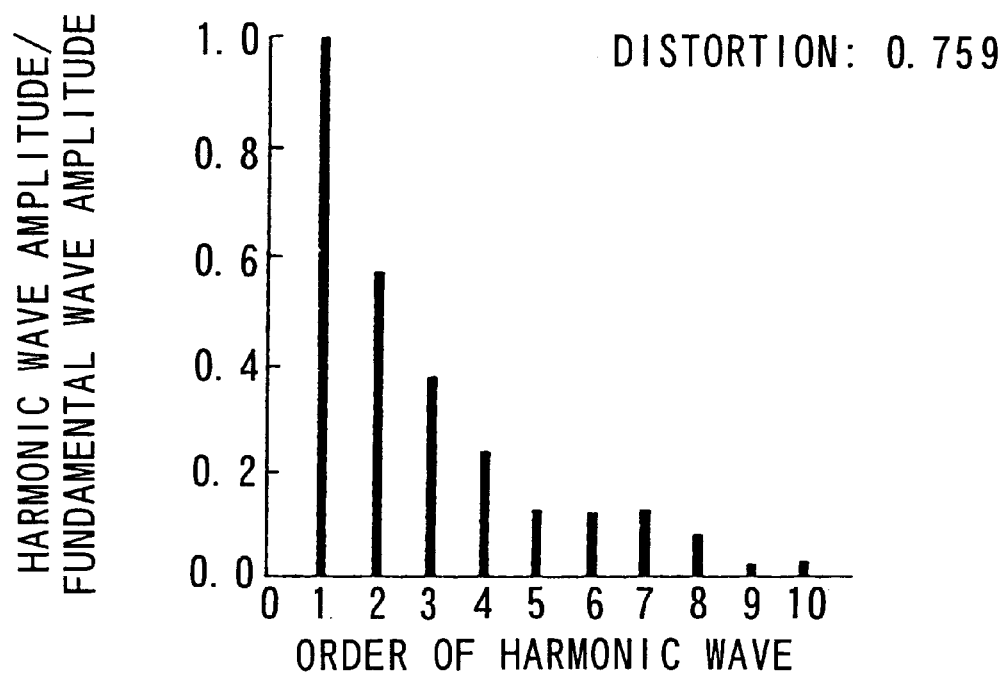
FIG. 12 is a graph showing an example of the frequency line spectrum of a Xuan mai or violent pulse.

FIG. 10 is a graph showing an example of the frequency spectrum of a normal pulse; FIG. 11 shows an example of the frequency spectrum of a smooth pulse; and FIG. 12 shows an example of the frequency spectrum of a violent pulse. As may be understood from these figures, the distortion value becomes greater in the progression from Xuan mai→Ping mai→Hua mai. Further, during exercise, distortion increases as the exercise intensity increases.

CPU 308 calculates distortion for the beat frequency components of the pulse waveform at rest and the pulse waveform during exercise, and judges that exercise intensity increases as the difference between these two values increases.

Note that distortion may be defined by the following equation.

$$\text{distortion} = (\sqrt{\Sigma(\text{harmonic wave amplitude})^2})/(\text{fundamental wave amplitude})$$

Embodiment 2

The second preferred embodiment of the present invention will now be explained.

The structure of the exercise intensity and exercise quantity measuring device according to this embodiment is fundamentally the same as that of the exercise intensity and exercise quantity measuring device according to the first embodiment.

However, this embodiment differs from the first embodiment in the addition of a new switch (start switch ST, indicated by the dashed line in FIG. 1) to input element 316.

The operation of this device is fundamentally the same as the operation of the device according to the first embodiment.

However, in the exercise intensity and exercise quantity measuring device according to the first embodiment, with the exception of when setting the upper and lower limit values for the pulse rate, the exercise quantity was constantly measured (i.e., the pulse rate was measured and the accumulated time duration was updated based on the result of this measurement). In contrast, the device according to the second embodiment differs in that once setting of the upper and lower limit values has been completed, then measurement of exercise quantity is initiated by depressing start switch ST. Then, to terminate measurement of exercise quantity, this start switch is pressed again.

Embodiment 3

The third embodiment of the present invention will now be explained.

The structure of the exercise intensity and exercise quantity measuring device according to this embodiment is basically the same as that of the exercise intensity and exercise quantity measuring device according to the first embodiment (see FIG. 1).

However, this embodiment differs in that the output signal from body motion sensor 302 is directly input to CPU 308.

The operation of the device according to this embodiment is basically the same as that of the exercise intensity and exercise quantity measuring device according to the first embodiment.

However, in the device according to the first embodiment, with the exception of when setting the upper and lower limit values for the pulse rate, the exercise quantity was constantly measured (i.e., the pulse rate was measured and the accumulated time duration was updated based on the result of this measurement). In contrast, in the device according to this embodiment, measurement of exercise quantity is carried out only when the level of the signal output from body motion sensor 302 is above a specific value.

This is done so that time duration accumulation as described above is not carried out in cases where pulse rate is rising due to factors other than exercise (such as psychological pressure, for example).

Modifications

Preferred embodiments of the present invention were explained above with reference to the accompanying figures. However the specific design of the present invention is not limited thereto. Rather, modifications such as described below are possible, provided that these remain within the intended scope of the invention.
(1) Modified method for specifying beat component
(1.1) Maximal design simplification In each of the preceding embodiment, the beat frequency component is specified according to the flow chart in FIG. 7. However, when the processing capacity of CPU 308 is not sufficient, then the processing for specifying the beat frequency component may be simplified as follows.

Figure 8:
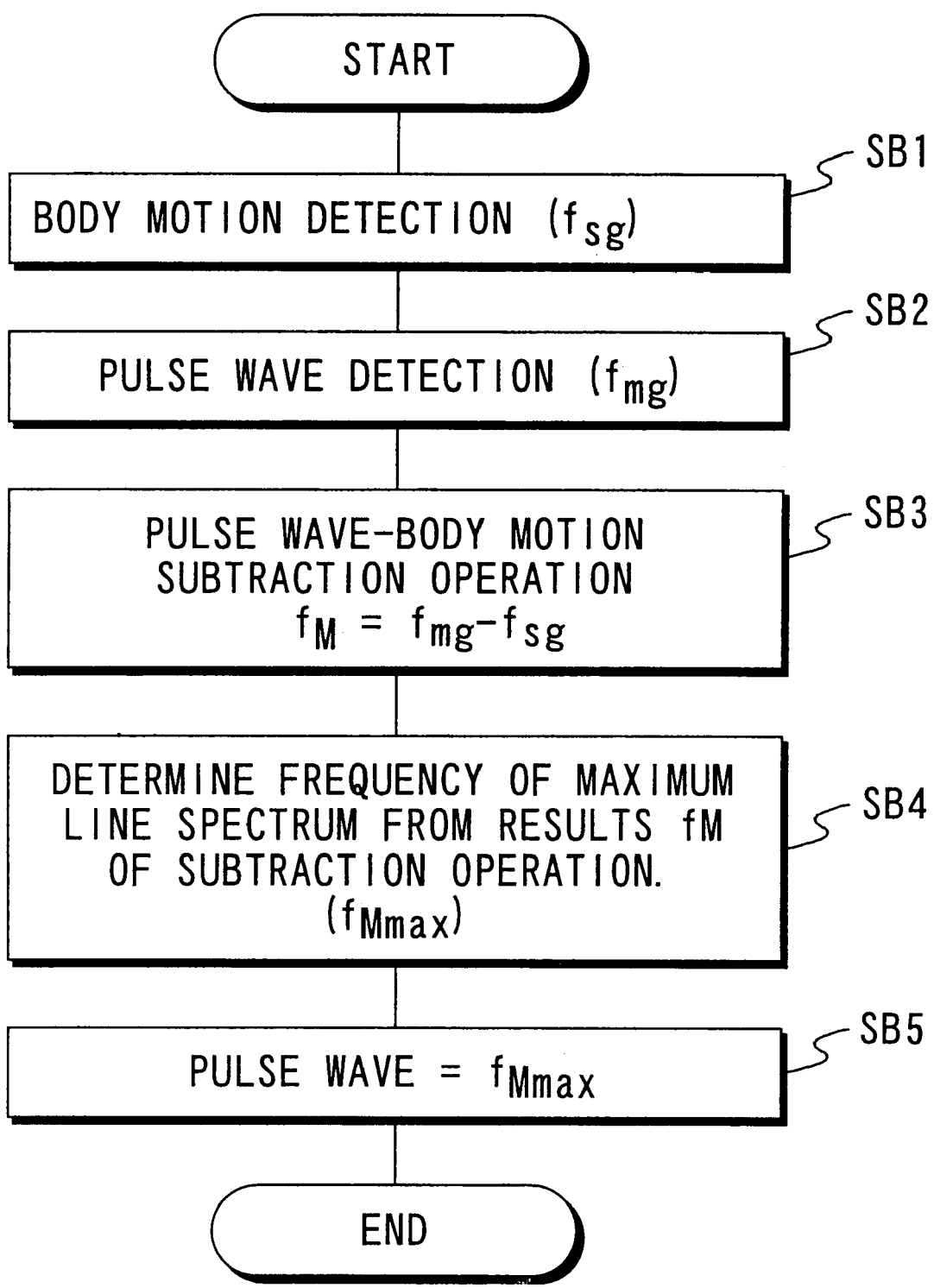
FIGS. 8 and 9 are flow charts showing examples of modifications of FIG. 7.

FIG. 8 is a flow chart showing an example in which the method for specifying the beat frequency component has been simplified.

In this figure, in step SB3, CPU 308 carries out a pulse wave-body motion subtraction operation (i.e., $f_M = f_{mg} - f_{sg}$), to extract the frequency component which is present only in the beat signal. In step SB4, CPU 308 specifies the maximum frequency component from the extracted pulse wave component $f_M$. The specified $f_{Mmax}$ is the beat frequency component. There is a difference in the change in the harmonic wave component in the beat component and the body motion component due to the exercise load, so that the change in the beat component is well expressed. This is caused by the change in heart functioning, and is well expressed in the change in stroke volume per beat (SV). Further, as is well known, beat rate increases as the exercise load becomes greater.
(1.2) Specifying the maximum component of the body motion component as the second harmonic wave In the preceding embodiments, the maximum component of the body motion component was initially assumed to be the second harmonic wave, and an investigation was carried out to determine whether or not this assumption was correct (steps SD2, SD4). The probability that this assumption was correct is viewed to vary according to conditions such as type of exercise (running, swimming, race walking, etc.), the movement of the user s body during the particular type of exercise, and the like. Accordingly, provided that the conditions are understood, then the probability that the assumption is correct becomes extremely high. In this case, the processing for verifying the assumption may be omitted.

Figure 9:
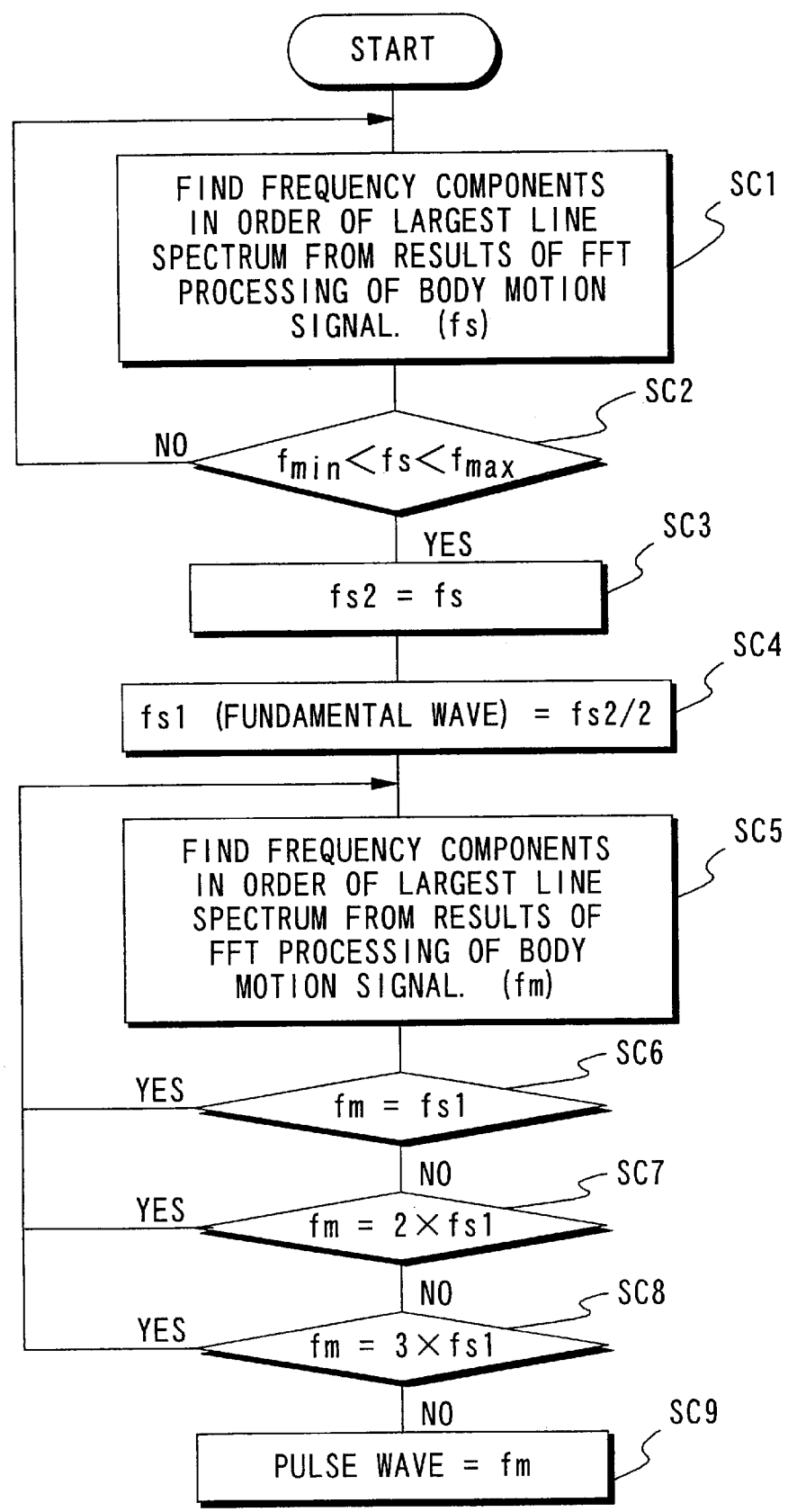

FIG. 9 is a flow chart showing an example in which the method for specifying the pulse wave component has been simplified based on this principle.

In steps SC1~SC3 in the example shown in this figure, CPU 308 specifies the frequency fs2 of the second harmonic wave from body motion sensor 302, which is relatively easily detected as a body motion component.

In the case where the exercise is running, for example, the $f_{min}$ shown in step SC2 is defined to be 2 Hz, i.e., the frequency which is the lower limit at which the second harmonic wave for running motion appears.

On the other hand, the $f_{max}$ shown in step SC2 is the frequency which is determined by the sampling rate for the A/D conversion. When the sampling frequency is set to 8 Hz, then, according to the sampling theorem, the maximum frequency at which the original waveform reappears is automatically determined to be 4 Hz.

The maximum line spectrum in this $f_{max}$ to $f_{min}$ range is specified as the second harmonic wave fs2 of the body motion component.

Next, in step SC4, CPU 308 obtains frequency fs1 of the fundamental wave of body motion.

In steps SC5~SC8, CPU 308 removes the pulse wave component which coincides with the fundamental wave (fs1), second harmonic wave (2×fs1), and third harmonic wave (3×fs1) of the body motion component from the spectrum detected by pulse wave sensor 301.

In step SC9, the maximum frequency component remaining after the above-described removal process is specified as the pulse wave fm.
(2) Modified method for estimating exercise intensity In the preceding embodiments, an estimation of exercise intensity was made based on the distortion in the pulse wave. However, it is also acceptable to estimate exercise intensity according to the type of pulse wave. This will be explained in greater detail below.

Figure 13:
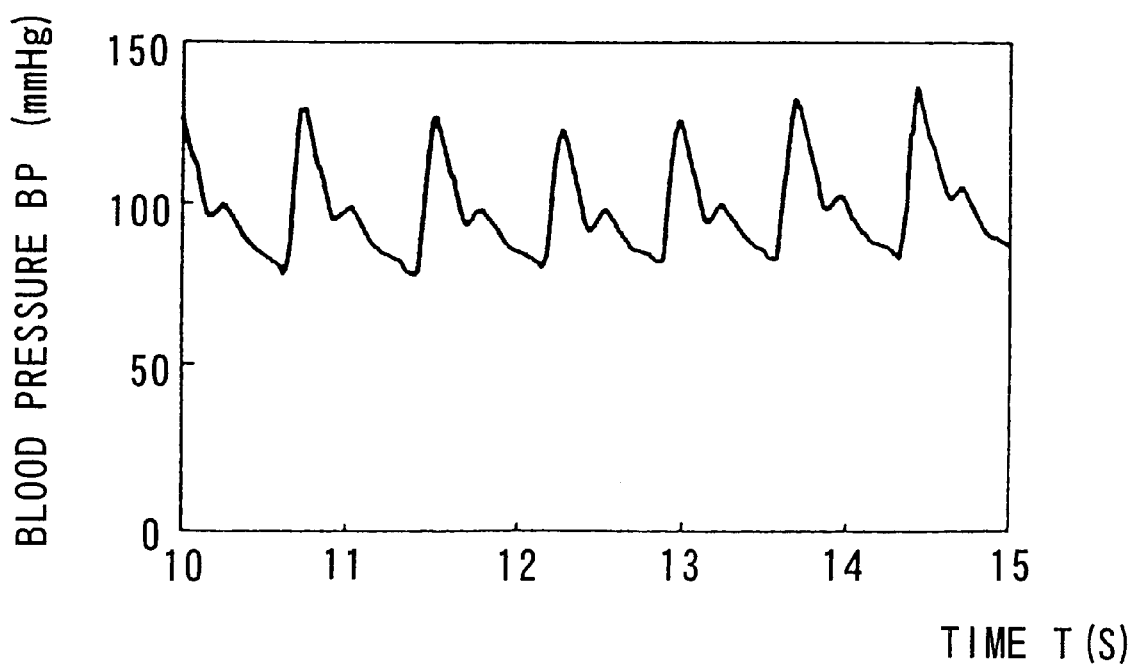
FIG. 13 is a waveform diagram showing an example of a Ping mai.
Figure 14:
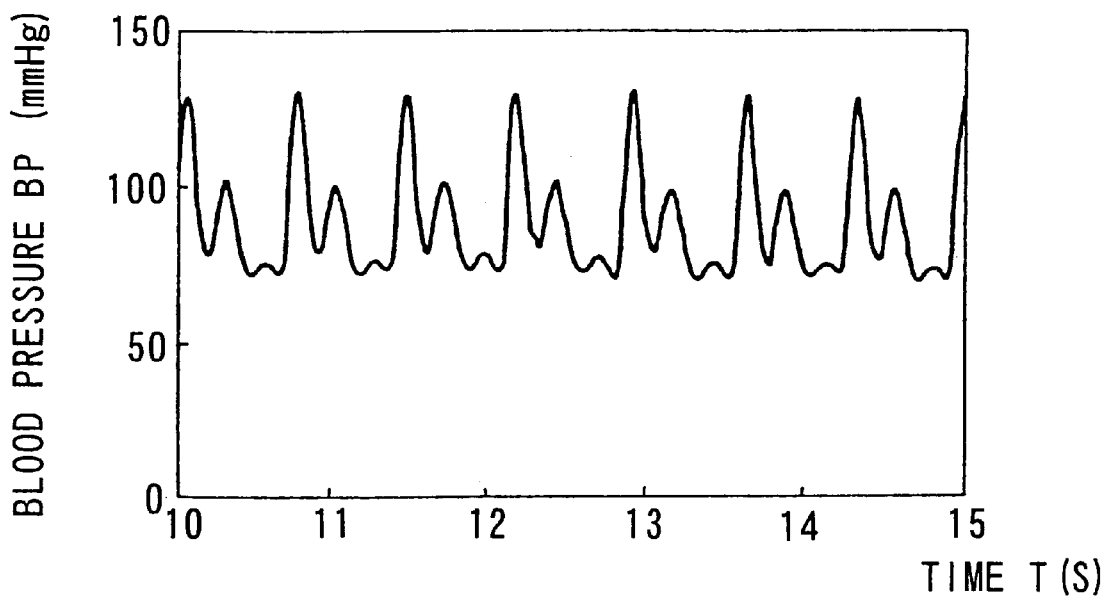
FIG. 14 is a waveform diagram showing an example of a Hua mai.
Figure 15:
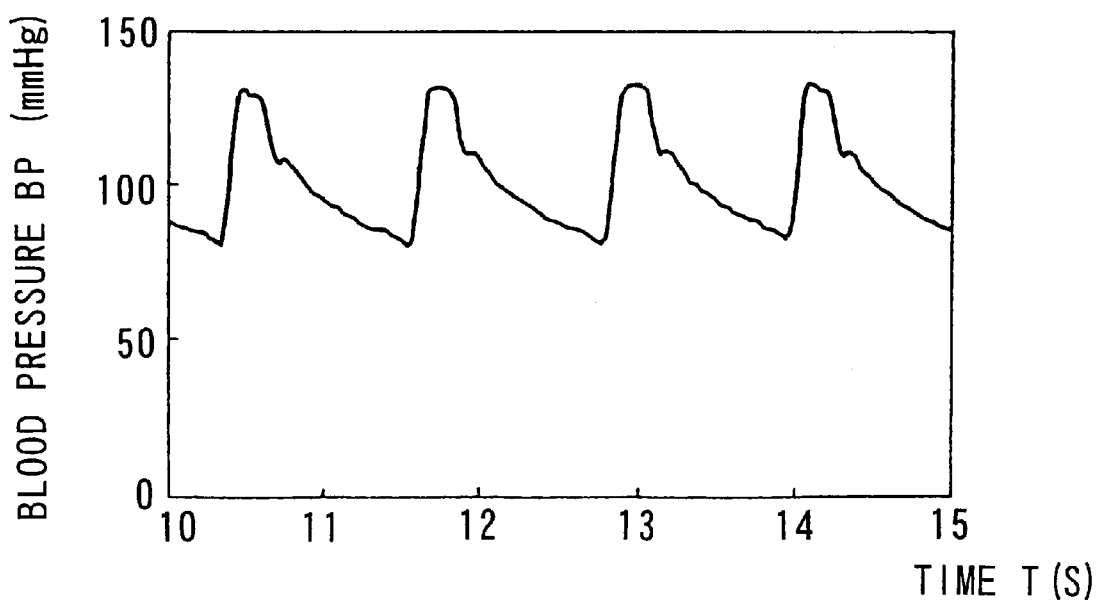
FIG. 15 is a waveform diagram showing an example of a Xuan mai.

FIG. 13 is a waveform diagram showing an example of a Ping mai. FIG. 14 shows an example of a Hua mai. FIG. 15 shows an example of a Xuan mai. As may be understood from these figures, the amplitude of blood pressure differs for each of these waves.

CPU 308 compares the size of the amplitudes of the harmonic components for the pulse waveform at rest, and determines whether the pulse waveform at rest is a Ping mai, Hua mai, or Xuan mai. For example, CPU 308 compares the amplitudes of the second harmonic wave and the third harmonic wave. If the second harmonic wave is larger, CPU 308 determines that the wave is a Ping mai, while if the third harmonic wave is larger, CPU 308 determines that the wave is a Hua mai. Further, if the amplitude of the second harmonic wave is roughly less than half the amplitude of the first harmonic wave, then CPU 308 determines that the wave is a Xuan mai.

Similarly, CPU 308 compares the size of the amplitudes of each of the harmonic wave components for the pulse waveform during exercise, and determines whether the pulse waveform during exercise is a normal, smooth, or Xuan mai.

Next, CPU 308 measures the exercise intensity according to the waveform classification of each of the preceding waves.

(3) Modified method for providing notification of exercise intensity (3.1) Notification using visual sense In the preceding embodiments, the exercise intensity and exercise quantity were displayed as numeric values on display element 313. The present invention is not limited thereto, however.

Figure 19:
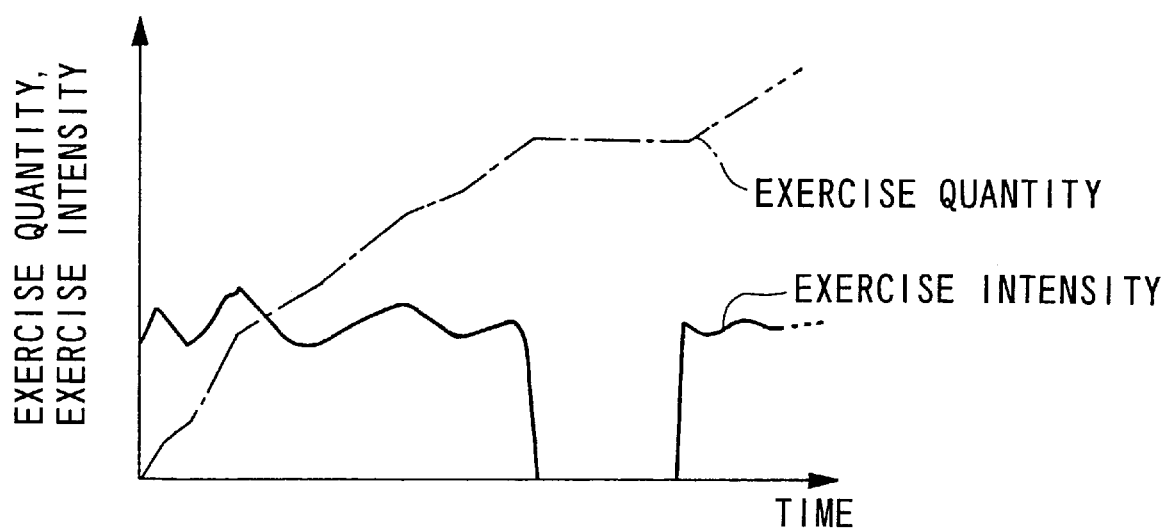
FIGS. 19 and 24 are figures showing examples of modifications of the arrangement for displaying exercise intensity and exercise quantity.
Figures 20, 21:
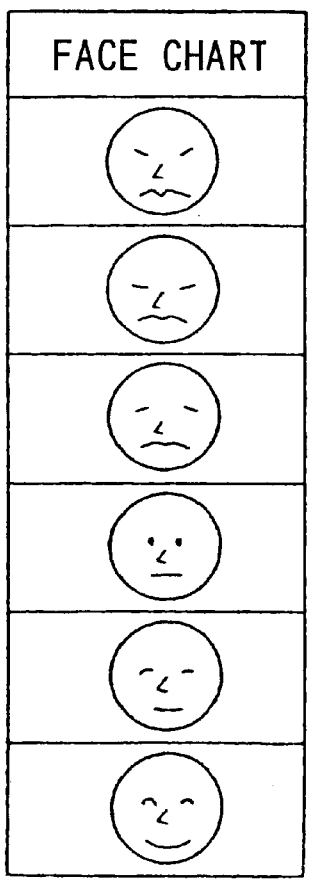

For example, as shown in FIG. 19, it is acceptable to display the past and current values for exercise intensity and exercise quantity in the form of a graph. Moreover, a face chart such as shown in FIG. 20 may be employed to indicate whether these values are within the appropriate range.

(3.2) Notification using other than visual sense

In addition to employing display element 313 (liquid crystal display) as the method for providing notification of exercise intensity, etc., it is also acceptable to provide notification which relies on the senses of hearing or touch. For example, in the case where employing a notification means which relies on the sense of hearing, a buzzer may be sounded when there is a danger due to placing an excessive load on the body. Where employing a notifying means which relies on the sense of touch, a form memory alloy may be provided projecting outward from the rear surface of a main body 11 (see FIG. 2), with electricity passed through this form memory alloy when there is a danger present due to an excessive load being place on the body. Alternatively, a vibration alarm is conventionally known which communicates a vibration to the user s body by rotation of an eccentric load. This vibration alarm may be provided separately or in a unitary manner with main body 11, with electricity passed through the vibration alarm when the load on the body becomes excessive. In addition, a concavity may be formed in a portion of the inner side of the bottom surface of the main body 11 having a thickness of 70 μm as shown in FIG. 16. A piezoelement PZT is then attached to this concavity. When an alternating current of a suitable frequency is impressed on this piezoelement, piezoelement PZT vibrates, with this vibration communicated to the user. Accordingly, if an alternating current is impressed when there is danger due to an excessive load being placed on the body, then it is possible to provide tactile notice of exercise intensity. Additionally, piezoelement PZT may have a thickness of 100 μm, with a diameter length which is 80% of the length of the diameter of the concavity.

(4) Modified method for measuring $Vo_{2max}$

In addition to the direct method cited above, various other methods may be considered for estimating $Vo_{2max}$, including a measurement method employing respired gas components, or a method in which the estimate is obtained from the lactic acid threshold.

The respired gas method cited here is a method for estimating $Vo_{2max}/wt$ from the $CO_2$ present in respiration and the power under maximum effort exercise, while the lactic acid threshold method estimates $Vo_{2max}/wt$ from the power under maximum effort exercise and lactic acid in the blood.

In addition to a method using up switch U and down switch D, other methods are available for inputting $Vo_{2max}$, including the method of providing a small ten-key, or a method in which input of $Vo_{2max}$ is carried out by communication from a personal computer or other device (either wireless or wired).

Further, the pulse rate table in FIG. 17 is merely a single example. Accordingly, the relationship between pulse rate and $Vo_{2max}$ in the preceding embodiments is not limited thereto.

(5) Notification of exercise plan

After the user has input $Vo_{2max}$ in the preceding first through third embodiments, the user may be notified of an exercise plan based on the input $Vo_{2max}$. The details of this will now be explained. First, in order to provide notification of an exercise plan, it is necessary to know the user s optimal exercise intensity, duration of exercise per exercise session, and exercise frequency during a specific period of time.

As discussed above, the optimal exercise intensity is the exercise intensity corresponding to 50% of $Vo_{2max}$. Thus, this value can be directly determined once $Vo_{2max}$ is obtained. Further, if the typical person is taken as the subject, then a suitable duration of exercise per session is 20 min, while a suitable exercise frequency is 40~50%, (i.e., 4 to 5 days out of a 10-day period).

Figure 22:
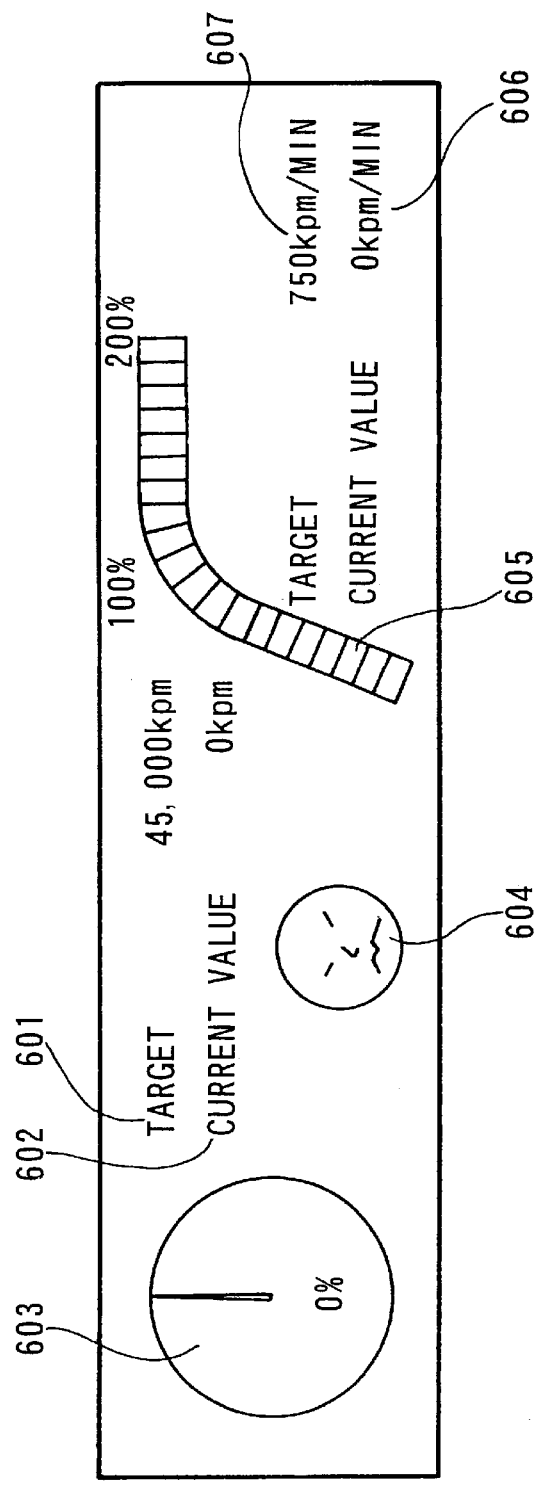

Accordingly, in this modification, once the $Vo_{2max}$ has been obtained, then an exercise target screen such as shown in FIG. 21 is displayed on display 313. From the example in this figure, it may be understood that exercise of 750 kpm/min, 3 times a week for 20 minutes at a time, is suitable. Here, the screen shown in FIG. 22 is displayed in display 313 when the user performs a specific manipulation.

In the figure, 601 is an exercise quantity target value display which displays a target value for the user with respect to the exercise quantity per week. From the preceding example, the exercise quantity target value would be [750[kpm/min]×20[min]×3[times]=45000[kpm]]. Accordingly, this value is displayed on the display. 602 indicates an exercise quantity current value display which displays the cumulative value for the quantity of exercise performed by the user over the past week. However, the example shown in the figure assumes the state immediately after the user has initiated the device according to this modification for the first time, and obtained the $Vo_{2max}$. Therefore, a [0] is displayed on exercise quantity current value display 602.

Next, 603 indicates a bar graph display which displays the exercise quantity current value with respect to the exercise quantity target value as a percentage proportion thereof. 604 is a face chart display which displays a face chart in accordance with the exercise quantity current value-to-exercise quantity target value proportion. 607 is an exercise intensity target value display which displays the exercise intensity target value (750 [kpm/min]) obtained previously. 606 is an exercise intensity current value display which displays the current value of exercise intensity. The example shown in this figure assumes that the user has stopped, so that exercise intensity current value display 606 displays a [0].

Next, 605 is an exercise intensity meter wherein there are disposed 20 LEDs at intervals of 10% within the range of [0%]~[200%]. By means of the illumination of these LEDs, the proportion of the exercise intensity current value with respect to the exercise intensity target value is displayed. In the example shown in this figure, the exercise intensity current value is [0], so that none of the LEDs are illuminated. From among the LEDs which compose exercise intensity meter 605, those corresponding to [10~70%] are yellow, those corresponding to [80~120%] are blue, and those corresponding to [130% or higher] are red.

Figure 23:
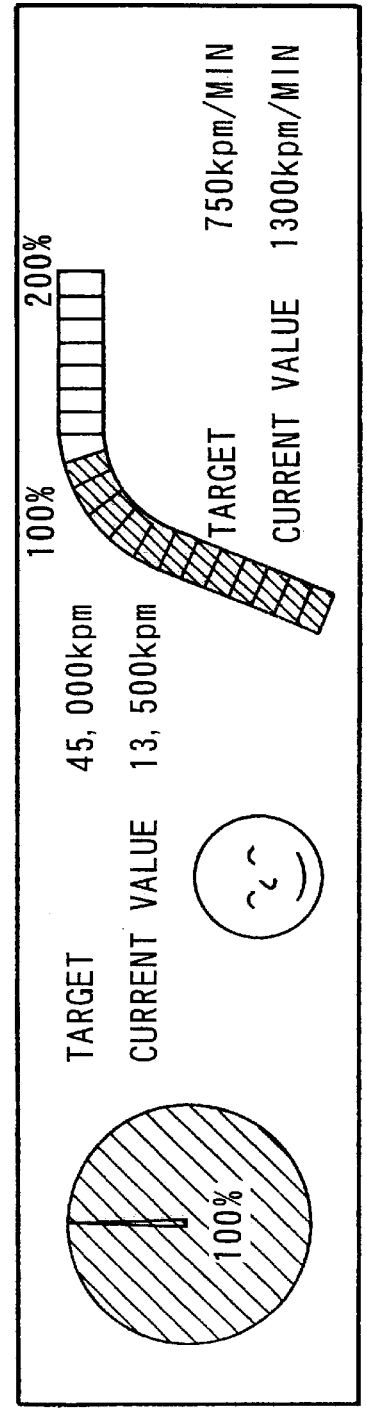

Next, an example of the display in the state where the user is carrying out exercise of a given degree is shown in FIG. 23. The exercise quantity current value in the example shown in the figure is [13500], so that [30%] of the exercise quantity target value has been reached. Accordingly, a bar graph corresponding to this is displayed on bar graph display 603, and a face chart displayed on face chart display 604 is changed in accordance to the proportion of the target value which has been achieved.

On the other hand, the exercise intensity current value is [1300], which greatly exceeds the exercise intensity target value of [750]. Accordingly, a number of red LEDs from among those provided to exercise intensity meter 605 are illuminated. Accordingly, the user is able to know that the intensity of exercise is too great by looking at the display.

Figure 24:
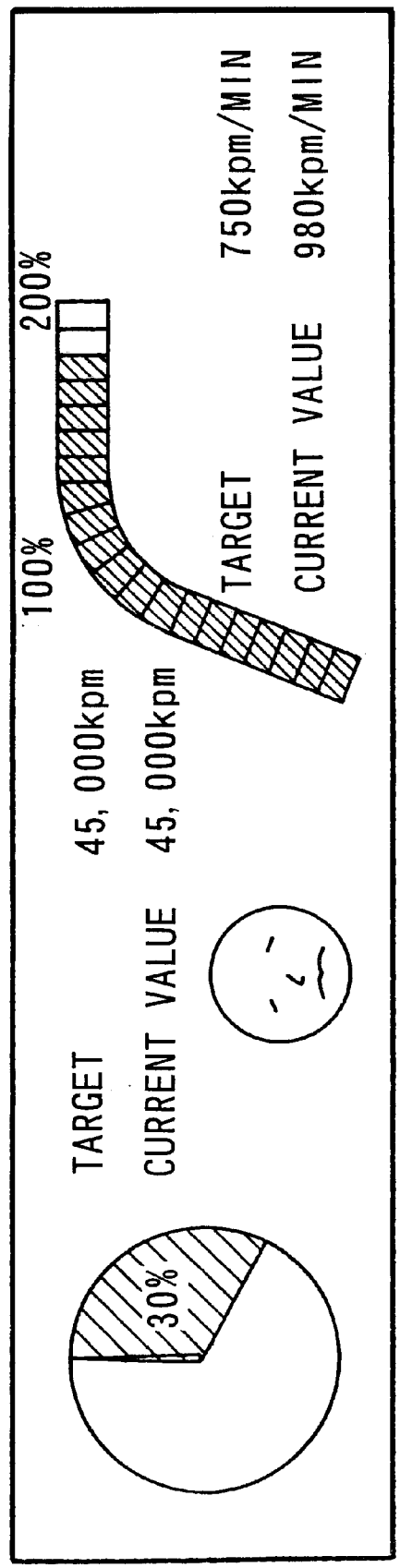

Next, the suitable state for the user s exercise quantity and exercise intensity is shown in FIG. 24. In this figure, the exercise quantity current value is [45000[kpm]], so that the exercise quantity target value has been reached. Accordingly, the displays on the bar graph display 603 and the face chart display 604 correspond to this state. Further, the exercise intensity current value is [980kpm/min], which is within ±20% of the exercise intensity target value. Thus, the corresponding green LEDs in exercise intensity meter 605 are illuminated.

In the example for this modification, the exercise quantity is recorded each day, extending over the past 7 days, and this cumulative result is displayed as the exercise quantity current value. Further, at a specific time (for example, 12 midnight), the data for exercise quantity from the oldest day is discarded, and the exercise quantity data from the new day is used in place thereof.

The above example employed a 7 day period for the interval over which the exercise quantity data is added up. However, this interval could also be 10 days or the like, for example. In other words, the user is free to set this interval. Accordingly, the user may set a specific interval such as [3 months], and then be able to carry out training by setting an exercise quantity targeted for that interval.

(6) Other modifications

In addition to FFT, other methods may be employed for the frequency analysis method carried out by CPU 308, such as the maximum entropy method, wavelet conversion method or the like.

Further, the site for detecting the pulse is not limited to the finger. Rather, provided that the pulse wave can be measured, other sites (such as the ear, for example) are also acceptable.

Further, the site for detecting the pulse is not limited to the finger. Rather, provided that the pulse wave can be measured, other sites (such as the ear, for example) are also acceptable.

Similarly, an acceleration sensor employed as body motion sensor 302 is not limited to attachment to the arm only. Rather, the acceleration sensor may be attached anywhere on the user s body, so that a measurement of the pitch may be carried out from the change in the acceleration.

Further, the method of attachment for the sensor in this case is not limited to finger belt 13 shown in FIG. 2. Namely, a finger sock, arm belt or the like may also be employed.

In addition, it may also be considered to correct the pulse rate read out from the pulse rate table according to factors such as the age of the user, the surrounding temperature obtained via a temperature sensor (not shown), suitable exercise intensity for the body condition at that time, etc.

In addition, in the preceding embodiment, the upper and lower limit values were set to be within ±20% of the read out pulse rate, however, other widths therefor may be considered.

A photoelectric sensor may be employed for pulse wave sensor 301 and body motion sensor 302.

Further, in each of the preceding embodiments, the pulse rate table recording element 315 was composed of ROM. However, in addition, it is also possible to employ a nonvolatile memory ($E^2PROM$, flash memory, battery backed-up RAM, etc.) which is write-capable. In this case, the contents of the pulse rate table shown in FIG. 17 are occasionally written over in response to improvement in the user s exercise capacity.

What is claimed:

1. An exercise intensity measuring device, wherein said device detects a pulse waveform of a user and obtains the exercise intensity for exercise currently being performed by the user from the fundamental wave and the harmonic wave of the pulse waveform.

2. An exercise intensity measuring device, comprising:

detecting means for detecting the pulse waveform of a user;

storing means for storing the pulse waveform detected by said detecting means when the user is at rest;

estimating means for estimating exercise intensity on the basis of the pulse waveform stored in said storing means and the pulse waveform detected by said detecting means during exercise; and notifying means for providing notification of the exercise intensity obtained by said estimating means.

3. An exercise intensity measuring device according to claim 2, wherein said detecting means further comprises:

pulse wave detecting means for detecting the pulse waveform by means of a pulse wave sensor;

body motion detecting means for detecting body motion by means of a body motion sensor;

frequency analyzing means for analyzing the frequency of the signals output from said pulse wave detecting means and said body motion detecting means; and pulse wave component extracting means for extracting a pulse wave component from the results obtained after said frequency analysis.

4. An exercise intensity measuring device according to claim 2, wherein said estimating means estimates said exercise intensity based on distortion in the pulse waveform.

5. An exercise intensity measuring device comprising:

detecting means for detecting the pulse waveform of a user;

storing means for storing the pulse waveform detected by said detecting means when the user is at rest;

estimating means for estimating exercise intensity on the basis of the pulse waveform stored in said storing means and the pulse waveform detected by said detecting means during exercise; and notifying means for providing notification of the exercise intensity obtained by said estimating means;

wherein said estimating means measures exercise intensity based on the size of the amplitude of each harmonic wave component of the pulse waveform.

6. An exercise quantity measuring device, comprising:

pulse rate setting means for setting the appropriate limits for the pulse rate of a user during exercise, based on the maximal oxygen uptake quantity;

pulse rate measuring means for measuring the pulse rate of the user;

accumulating means for accumulating the time duration in which the pulse rate measured by said pulse rate measuring means is within the limits set by said pulse rate setting means; and notifying means for providing notice of the results of the accumulating operation performed by said accumulating means.

7. An exercise quantity measuring device according to claim 6, wherein said pulse rate setting means comprises:

storing means for storing the correlation between maximal oxygen uptake quantity and the pulse rate;

input means for inputting the maximal oxygen uptake quantity obtained in advance;

read out means for reading out from said storing means the pulse rate corresponding to the maximal oxygen uptake quantity which was input by said input means;

correcting means for correcting said read out pulse rate; and calculating means for calculating limits of a specific width between said corrected pulse rate.

8. An exercise quantity measuring device according to claim 7, wherein said maximal oxygen uptake quantity is a value estimated by a direct method.

9. An exercise quantity measuring device according to claim 7, wherein said maximal oxygen uptake quantity is a value estimated from respiratory components.

10. An exercise quantity measuring device according to claim 7, wherein said maximal oxygen uptake quantity is a value estimated on the basis of a lactic acid threshold.

11. An exercise quantity measuring device according to claim 7, wherein:

said storing means stores said correlation for each sex;

said input means inputs the sex of the user, in addition to said maximal oxygen uptake quantity; and said read out means reads out from said storing means the pulse rate corresponding to said input sex and maximal oxygen uptake quantity.

12. An exercise quantity measuring device according to claim 7, wherein said pulse rate measuring means comprises:

detecting means for detecting the pulse wave and body motion of the user;

frequency analyzing means for analyzing the frequency of the body motion signal and the pulse wave signal detected by said detecting means;

extracting means for extracting the pulse wave frequency components on the basis of the pulse wave signal and body motion signal which were subjected to frequency analysis by said frequency analysis means; and pulse rate calculating means for calculating the pulse rate from the pulse wave frequency components extracted by said extracting means.

13. An exercise quantity measuring device according to claim 12, wherein said detecting means comprises a pressure sensor and an acceleration sensor.

14. An exercise quantity measuring device according to claim 12, wherein said detecting means comprises photoelectric sensors.

15. An exercise quantity measuring device according to claim 7, further comprising instructing means for outputting an initiation instruction and a termination instruction, said accumulating means initiating said accumulating operation according to said initiation instruction and terminating said accumulating operation according to said termination instruction.

16. An exercise quantity measuring device according to claim 7, further comprising body motion detecting means for detecting the body motion of the user, said accumulating means carrying out said accumulating operation while the value detected by said body motion detecting means exceeds a prespecified value.

17. An exercise intensity measuring device, wherein said device detects a pulse waveform of a user and obtains the exercise intensity for exercise currently being performed by the user from harmonic wave components including a fundamental wave component of the pulse waveform.

18. An exercise intensity measuring device according to claim 17, comprising:

pulse wave component detecting means for detecting a pulse wave component of the pulse waveform of the user excluding a body motion component; and estimating means for estimating said exercise intensity on the basis of said pulse wave component detected by the pulse wave component detecting means.

19. An exercise intensity measuring device according to claim 18, wherein said estimating means estimates said exercise intensity on the basis of the harmonic wave components including the fundamental wave component of said pulse waveform excluding the body motion component.

20. An exercise intensity measuring device according to claim 2, further comprising:

first amplitude calculation means for calculating amplitude values of harmonic wave components including a fundamental wave component of the pulse waveform in said storing means:

first comparison means for comparing said amplitude values calculated by said first amplitude calculation means with one another;

first classifying means for classifying the pulse waveform in said storing means according to the comparison by said first comparison means;

second amplitude calculation means for calculating amplitude values of harmonic wave components including a fundamental wave component of the pulse waveform detected by said pulse waveform detecting means during exercise;

second comparison means for comparing said amplitude values calculated by said second amplitude calculation means with one another; and second classifying means for classifying the pulse waveform detected by said pulse waveform detecting means during exercise according to the comparison by said second comparison means, said estimating means estimating said exercise intensity in accordance with the classification results by said first and second classifying means.

21. An exercise intensity measuring device according to claim 3, further comprising:

storing means for storing the pulse wave component extracted by said pulse wave component extracting means when the user is at rest; and wherein said estimating means estimates exercise intensity on the basis of a comparison of said pulse wave component stored in said storing means and said pulse wave component extracted during exercise.

22. An exercise intensity measuring device according to claim 2, wherein said estimating means further comprises:

first distortion-factor-calculation means for calculating a first distortion factor in the pulse waveform in said storing means;

second distortion-factor-calculation means for calculating a second distortion factor in the pulse waveform detected by said detecting means during exercise; and comparison means for comparing said first and second distortion factors, said estimating means estimating said exercise intensity on the basis of the comparison by said comparison means.

* * * * *